(12) United States Patent
Ossart

(10) Patent No.: US 6,596,507 B2
(45) Date of Patent: Jul. 22, 2003

(54) DEVICE AND METHOD FOR DETERMINING CHARACTERISTIC OF A BIOMASS

(75) Inventor: Frédéric Ossart, Nimes (FR)

(73) Assignee: Nanotec Solution, Nimes (FR)

( * ) Notice: Subject to any disclaimer, the term of this patent is extended or adjusted under 35 U.S.C. 154(b) by 0 days.

(21) Appl. No.: 10/018,004

(22) PCT Filed: Apr. 13, 2001

(86) PCT No.: PCT/FR01/01166

§ 371 (c)(1),
(2), (4) Date: Dec. 14, 2001

(87) PCT Pub. No.: WO01/79828

PCT Pub. Date: Oct. 25, 2001

(65) Prior Publication Data

US 2003/0070942 A1 Apr. 17, 2003

(30) Foreign Application Priority Data

Apr. 14, 2000 (FR) .............................................. 00 04808

(51) Int. Cl.⁷ ................................................. C12Q 1/02
(52) U.S. Cl. ............................... 435/29; 435/4; 435/34; 435/283.1; 435/285.2; 435/287.1
(58) Field of Search ...................... 435/29, 34, 283.1, 435/285.2, 287.1, 4

(56) References Cited

FOREIGN PATENT DOCUMENTS

| | | |
|---|---|---|
| EP | 0 281 602 | 9/1988 |
| WO | WO 88 02115 | 3/1988 |
| WO | WO 92 16835 | 10/1992 |
| WO | WO 93 14402 | 7/1993 |
| WO | WO 01/79828 A1 * | 10/2001 |

OTHER PUBLICATIONS

D. Kell et al., "Dielectric estimation of microbial biomass using the Aber Instruments Biomass Monitor", *Trends in Biotechnology*, vol. 16, No. 4, Apr. 1998, pp. 149–150.

H.P. Schwan et al., "Four–Electrode Null Techniques for Impedance Measurement with High Resolution", *The Review of Scientific Instruments*, vol. 39, No. 4, Apr. 1968, pp. 481–484.

* cited by examiner

*Primary Examiner*—Louise N. Leary
(74) *Attorney, Agent, or Firm*—Young & Thompson

(57) ABSTRACT

A device for determining the characteristics of a biomass, includes: a probe (S,S') including electrodes, two or four in number, for injecting a current into a medium containing biological cells and for reading the voltage applied to the medium, and a resistance for measuring the injected current; a conditioning unit (10) including an alternating voltage generator (112) and a circuit (200) processing current and voltage measuring signals, so as to deliver signals (C,G) respectively of measurement of the capacity and conductance of the medium. The conditioning unit (10) includes a zero method measuring bridge (150) automatically controlled to deliver the signals (C,G) of measurement of the medium capacity and conductance. The invention is useful for characterizing media containing biological cells, in particular for controlling biological fermentation process.

29 Claims, 5 Drawing Sheets

FIG_1

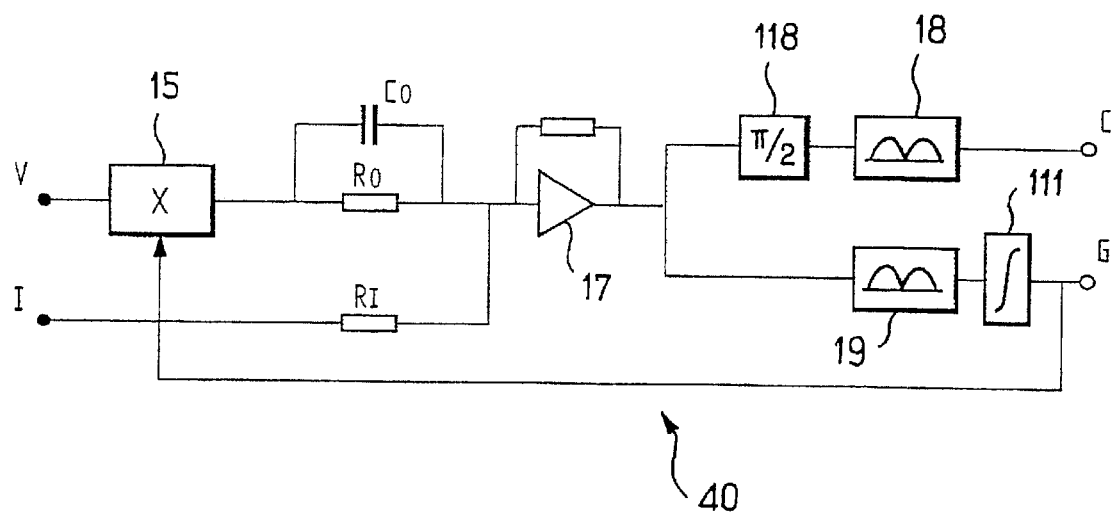
FIG_4

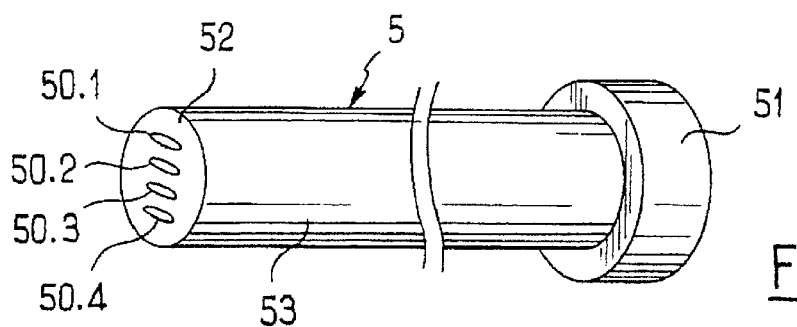
FIG_5
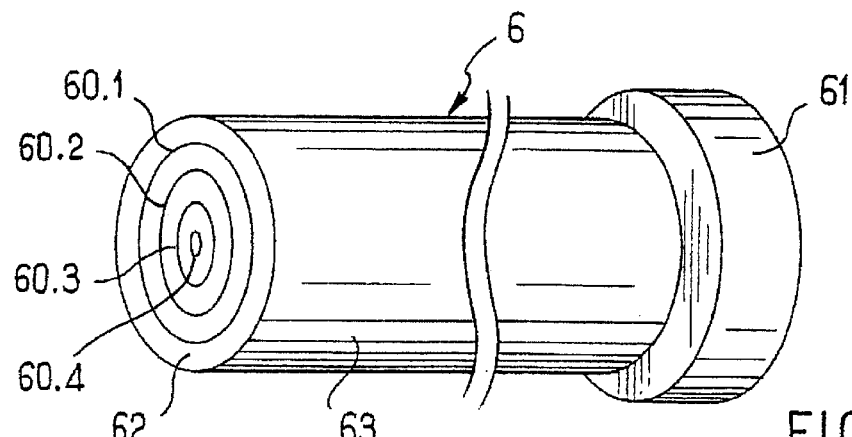
FIG_6
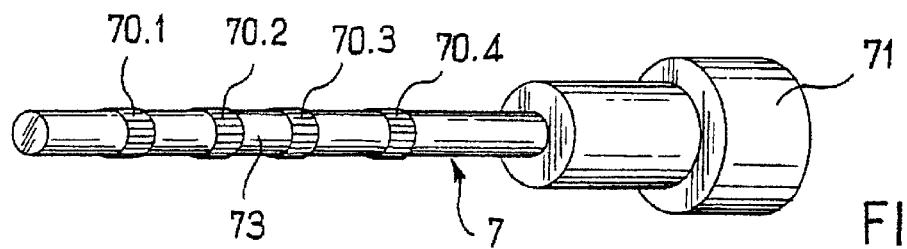
FIG_7
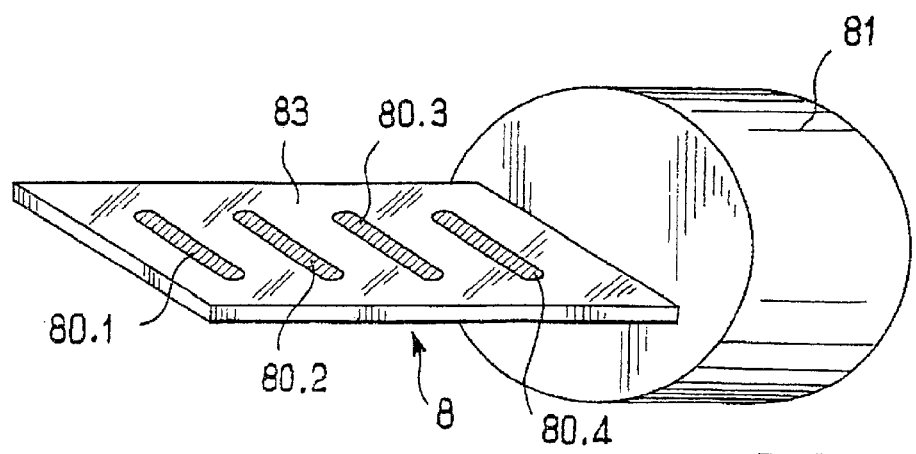
FIG_8

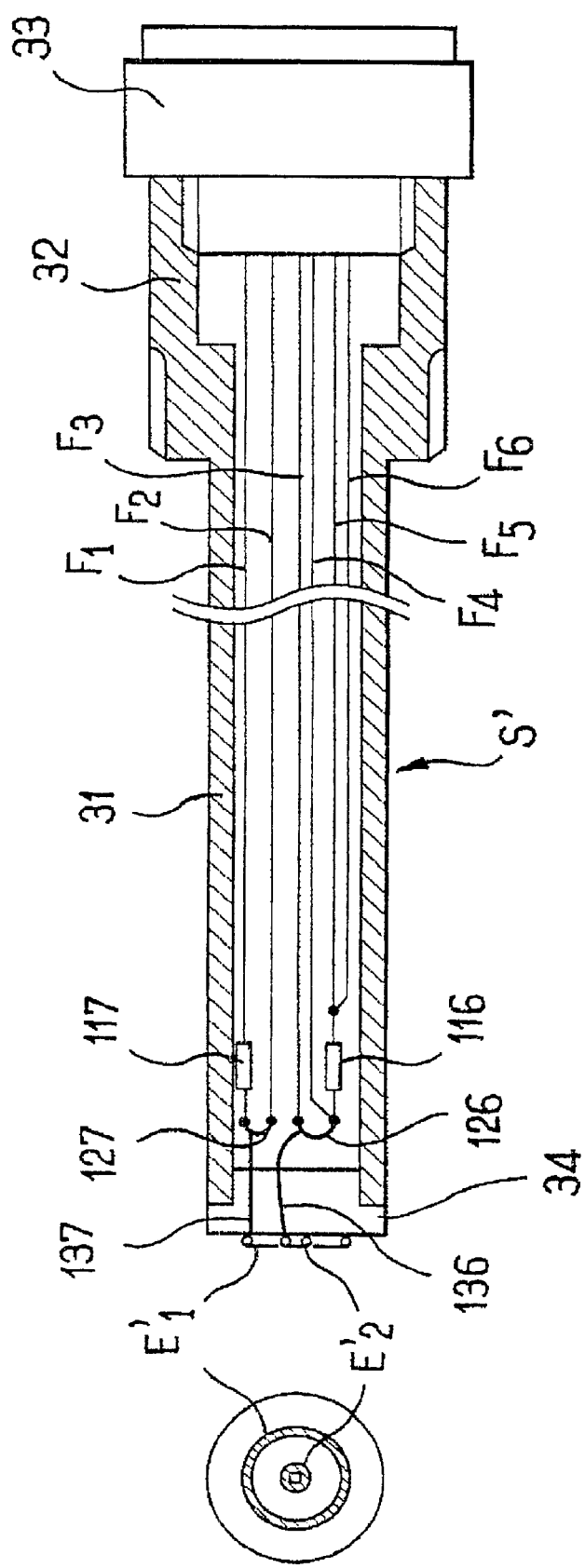
FIG_9

DEVICE AND METHOD FOR DETERMINING CHARACTERISTIC OF A BIOMASS

CROSS-REFERENCE TO RELATED APPLICATIONS

This is a 371 national stage application of PCT International application PCT/FR01/01166, filed Apr. 13, 2001.

The present invention relates to a device for determining characteristics of a biomass, that is to say of all media composed of biological cells. It also relates to a method used in this device.

A real time estimation of the characteristics of the biomass is essential for the optimum control of fermentation processes used in the food production, pharmaceutical and chemical industries and in biotechnologies. For a description of the general principle of the real-time estimation of a biomass, it will be possible to refer usefully to the article "Dielectric permittivity of microbial suspensions at radio frequencies: a novel method for the real-time estimation of microbial biomass" by C. M. Harris et al., published in the review "Enzyme Microb.technol., Volume 9, March 1987.

The document EP0281602 divulges an equipment for determining a biomass, comprising mutually spaced electrodes provided for being placed in the medium in electrical contact with the latter; and means for generating a signal dependent on the capacity between the electrodes, at a predetermined frequency or in a predetermined frequency range between 0.1 MHz and 10 MHz.

These electrodes comprise a first pair of electrodes for injecting current into the medium, surrounding a second pair of current electrodes, and are disposed in a probe including amplification means and connected to an electronic conditioner.

This conditioner comprises means for applying an alternative voltage, at the predetermined frequency, across the current electrodes, means for supplying a current signal indicative of the instantaneous current in the current electrode circuit, means for providing a voltage signal indicative of the instantaneous voltage at the terminals of the voltage electrodes; and means for determining the ratio between the value of the voltage signal and the value of a component in quadrature of the current signal, or vice-versa, in order to provide a signal dependent on the capacity.

However, this signal is necessarily also dependent on the frequency of the alternative voltage applied to the voltage electrodes, which implies maintaining this frequency constant during a measuring sequence.

The purpose of the invention is to propose a device for determining the electrical characteristics of a biomass, which makes it possible to obtain directly a signal representative of the capacity independently from the excitation frequency of the electrodes. Furthermore, another purpose of the invention is to obtain a device for determining electrical characteristics which is provided with a passive measuring probe having no electronic amplification means.

Furthermore, there is a growing need for measuring devices making it possible to determine the state of freshness and preservation of food products with a basis of biological cells, such as slices of fish or ham, which are offered for consumption.

Said objectives are achieved with a device for determining characteristics of a biomass, comprising:

a probe provided for being applied to a medium containing biological cells, said probe comprising means for injecting a current into said medium, means for reading the voltage applied to said medium, and means for measuring the injected current, a conditioner comprising means for providing a galvanically isolated alternative voltage to be applied to said current injection means, and means for processing signals respectively representative of the current injected into said medium and of the voltage read by the voltage reading means, in such a way as to deliver measurement signals respectively of the capacity and of the conductance of said medium.

According to the invention, the processing means comprise:

a measuring bridge using the null method designed to process a signal representing the injected current and a signal representing the read voltage applied respectively to a reference branch and to two opposing branches, and means for automatically controlling this bridge on the basis of the conductance measurement signal.

Unlike the impedance measuring devices of the prior art using a measuring bridge using the null method in which the impedance to be measured is actually inserted, in the measuring device according to the invention, the measuring bridge using the null method is disposed downstream of circuits delivering signals respectively representing the injected current and the voltage at the terminals of the impedance to be measured. In this way isolation problems are solved because this arrangement allows a floating bridge circuit and a preliminary amplification of the measurement signals delivered by the probe.

In a particular embodiment, the measuring bridge comprises:

a reference branch including a reference resistor to which is applied the signal representing the injected current, a first opposing branch including an adjustable opposing resistor and a second opposing branch including an adjustable opposing capacitor, the signal representing the read voltage being applied on these opposing branches, and amplification means having their input connected to said reference and opposing branches and delivering a null measurement signal.

In a device according to the invention further comprising means for delivering a signal representing the voltage read by the voltage reading means and means of delivering a signal representing the current injected by the current injection means, the conditioner further comprises a first modulator inserted between the output of the means of delivering the signal representing voltage and the first opposing branch, this first modulator being controlled by the conductance measurement signal in such a way that the null measurement signal is substantially zero.

In a particular embodiment, the probe comprises four wires connecting the current injection means and the voltage reading means to four terminals of connection means for connecting with the conditioner, and two additional wires respectively connecting the terminals of a current measuring resistor disposed inside said probe to two other terminals of said connection means.

In a first embodiment, the current injection means comprise two current electrodes for injecting current into the medium and the voltage reading means comprise two voltage electrodes for reading the voltage applied to the medium.

The current measuring resistor is then inserted between one of the current injection electrodes and one of the wires of the probe is connected via the connection means to a floating earth of the conditioner. The probe furthermore preferably comprises a compensating resistor inserted between one wire of the probe and the other current injection electrode.

In a second embodiment, the current injection means and the voltage reading means are produced in the form of a pair of measuring electrodes comprising a first measuring electrode connected to both a first wire and a second wire of the probe and a second measuring electrode connected to both a third wire and a fourth wire of the probe.

This simplified embodiment can be envisaged when the measuring ranges and the sought accuracies permit it. The current measuring resistor can be inserted between the second measuring electrode and one of the wires of the probe connected via the connecting means to a floating earth of the conditioner, and the probe can further comprises a compensating resistor inserted between the first measuring electrode and a wire of the probe.

In both of said embodiments, the current measuring resistor is preferably disposed in the vicinity of the electrodes of the probe.

This particular arrangement of the measuring probe has as an advantage the fact that this probe can be entirely passive and not include an amplifier, unlike the probe described in the document EP0281602 which includes amplification electronics. It then becomes possible to design probes having a very small diameter, for example having a diameter of 12 mm.

Furthermore, the conditioner of the device according to the invention can be easily checked by replacing the measuring probe with a passive standard probe consisting of a resistor and a capacitor.

Several probe geometries can he envisaged within the context of the invention, both for the embodiment having four electrodes and for the embodiment having two electrodes. It is thus possible to provide a probe in which the electrodes are disposed on a flat support at the end of a cylindrical body of the probe and disposed substantially parallel with each other.

The electrodes can also consist of concentric annular elements, or they can even be disposed on a tubular body or on a substantially flat body.

The automatic control means can be designed to control the bridge on the basis of the capacity measurement signal. The conditioner then further comprises a second modulator inserted between the output of the means of delivering the signal representing voltage and the opposing capacitor, said second modulator being controlled by the capacity measuring signal in such a way that the null measuring signal is substantially zero.

In a practical embodiment of the device according to the invention, the processing means further comprise, at the output of the measuring bridge, a first channel and a second channel respectively, each one comprising synchronous detection means and first integrators delivering the capacity and conductance measurement signals respectively, these synchronous detection means being controlled by the output signal of oscillator means.

The probe comprises only passive components and is connected in a detachable manner to the conditioner. The conditioner further comprises a first differential amplifier and a second differential amplifier electrically connected to the probe and provided for delivering the current signal and the voltage signal respectively.

It should be noted that it is also possible to provide, within the context of the present invention, active probes including one or more active components of the conditioner.

According to another aspect of the invention, a method is proposed for determining characteristics of a biomass, used in the device according to the invention, comprising:

an injection of an alternative current, at a predetermined frequency into a medium containing biological cells, by current injection means, a measurement of the current injected into said medium, a measurement of the voltage at the terminals of voltage reading means disposed in the vicinity of the current injection electrodes, and a processing of the signals representing the current injected into said medium and the read voltage respectively, in such a way as to deliver measurement signals of the capacity and of the conductance respectively of said medium.

This method is characterised in that the processing of the current and voltage signals includes a null method using a measuring bridge comprising, on the one hand, a reference branch on which the signal representing the current is applied and, on the other hand, two opposing branches on which the signal representing the voltage is applied, these opposing branches respectively comprising an adjustable resistive component and an adjustable capacitive component, and this measuring bridge being automated to deliver a measurement signal of capacity and a measurement signal of the conductance of the medium.

Thus, in the present invention, the measurement of the resistance and of the capacity of the medium is determined by a null method, on the basis of the action that it is necessary to carry out in order to cancel out the real part and the imaginary part of the representation of the current passing through the biomass. With this measuring method, it is not necessary to control the amplitude of the voltage at the terminals of the transmitting electrodes, unlike the measuring method described in the document EP0281602 for which it is imperative to maintain the amplitude on the receiving electrodes constant.

For a description of the general principle of impendence measuring by the null method with the use of four electrodes, it will be possible to refer usefully to the article "Four-Electrode Null Techniques for Impedance Measurement with High Resolution" by H. P. SCHWAN and C. D. FERRIS in the publication "The Review of Scientific Instruments", Volume 39, No 4, April 1968.

The use of a measurement by the null method procures numerous advantages among which is the fact that the measurement of capacity is direct and does not depend on frequency. Furthermore, the measurement of capacity is not very sensitive to harmonics and procures a very good resolution.

The opposition is achieved by processing a voltage signal taken from the terminals of voltage measuring electrodes, via a reference resistor and an opposing capacitor. This opposition is carried out just at the output of differential measuring amplifiers respectively supplying a voltage signal and a current signal, and the opposition amplitude is automatically servo-controlled by means of modulators.

BRIEF DESCRIPTION OF DRAWINGS

Other features and advantages of the invention will furthermore appear in the following description. In the appended drawings, given by way of non-limitative examples:

FIG. 4 shows an alternative embodiment for determining capacity in a capacitive measuring device according to the invention;

FIG. 5 shows a first example of embodiment of a non-intrusive probe equipping a capacitive measuring device according to the invention, of the flat-ended type;

FIG. 6 shows a second example of embodiment of a non-intrusive probe equipping a capacitive measuring device according to the invention, of the annular type;

FIG. 7 shows a particular example of embodiment of a probe equipping a capacitive measuring device according to the invention, of the tubular type;

FIG. 8 shows another particular example of embodiment of a probe equipping a capacitive measuring device according to the invention, in which electrodes are disposed on a flat support; and FIG. 9 is a cross-sectional view of a second embodiment of a probe equipping a capacitive measuring device according to the invention, of the type having two electrodes.

Figure 1:
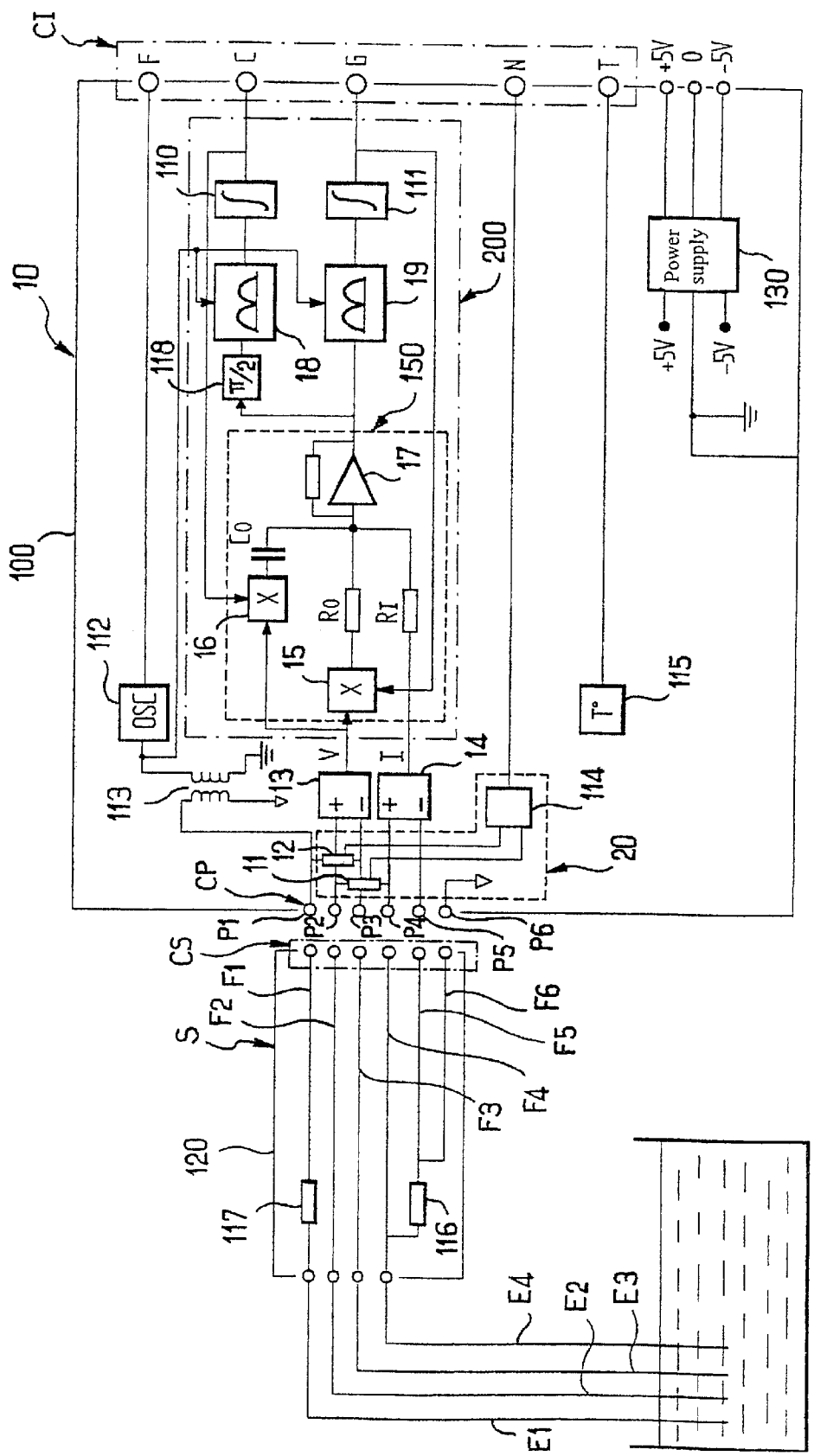
FIG. 1 is a block diagram of a particular example of embodiment of a capacitive measuring device according to the invention, equipped with an immersed probe.

There will now be described, with reference to FIG. 1, an example of embodiment of a determining device according to the invention equipped with a probe having four electrodes. The device 1 according to the invention comprises a measuring probe S and an electronic conditioner 10 to which this probe is connected. The conditioner 10 is enclosed in a shielded enclosure 100 respectively connected to the earth of said conditioner. The probe S is included in an enclosure 120 which is not necessarily shielded, the medium in which the electrodes are immersed providing a shield function.

The measuring probe S comprises two current injection electrodes E1, E4 between which are disposed two voltage measuring electrodes E2, E3. These electrodes E1–E4 are connected, respectively via connecting wires F1, F2, F3, F6 inside the probe S, to an electrical connector CS for connecting with the conditioner.

The measuring probe S further comprises two current measuring wires F4, F5 connected to the terminals of a measuring resistor 116 inserted between the current injection electrode E4 and the connecting wire F6. A resistor 117, providing an electronic balancing function, is inserted between the current injection electrode E1 and the connecting wire F1.

Figure 3:
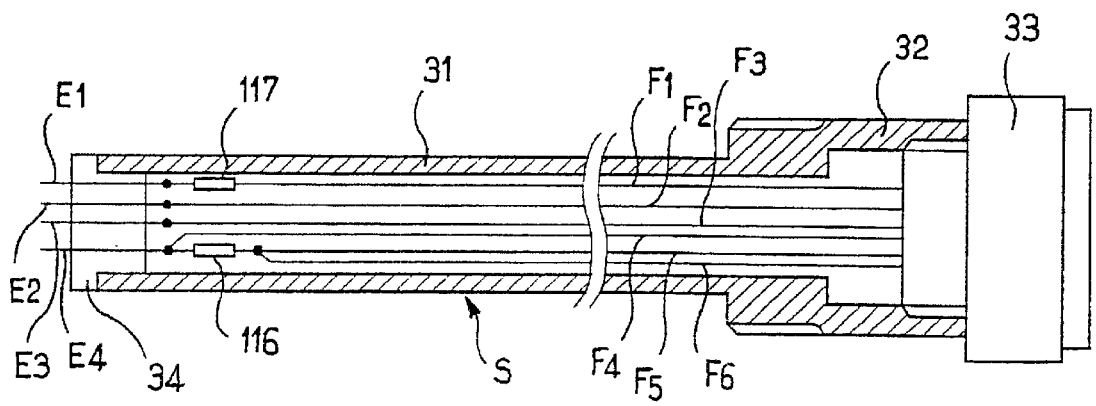
FIG. 3 is a cross-sectional view of a first embodiment of a probe equipping a capacitive measuring device according to the invention, of the type having four electrodes.

The connecting wires F1–F6 and the two resistors 116, 117 are for example disposed, with reference to FIG. 3, in a cylindrical enclosure 31 comprising at its free end an end-piece 34 supporting the four electrodes E1–E4 and at its other end a cylindrical base 32 comprising a threaded internal surface provided for receiving a connector 33 designed to be coupled with the measuring connector CP of the conditioner 10.

When the desired measuring ranges and accuracies so permit, it is possible to simplify the end of a probe equipping a capacitive measuring device according to the invention by using only two electrodes for measuring impedance, as illustrated in FIG. 9 in which the elements that are the same as those in FIG. 3 have the same references. In order to produce a probe having two electrodes S' of this type, it is possible for example to make use of the complete wiring of a probe having four electrodes such as the one shown in FIG. 3 by modifying it as follows: the first transmitting wire FE1 is connected by a first short-circuit 127 to the first receiving wire FE2, whilst the second transmitting wire FE4 is connected by a second short-circuit 126 to the second receiving wire FE3. The connection FE1–FE2 is connected to a first annular electrode E1' whilst the connection FE3–FE4 is connected to a second annular electrode E2' concentric with the first electrode E1' and surrounded by the latter, these two electrodes E1', E2' being disposed on the flat end of the probe S'.

Other probe geometries and structures can also be envisaged for equipping a capacitive measuring device according to the invention, as shown in FIGS. 5 to 8. Thus it is possible to provide, with reference to FIG. 5, a flat-ended probe 5 comprising at a first end of a tubular part 53 a flat support 52 comprising two transmitting electrodes 50.1, 50.4 and two receiving electrodes 50.2 and 50.3 and, at its second end, a connector 51. These four electrodes are substantially parallel with the support plane of the flat end and are substantially parallel with each other. This flat-ended probe 5 can be used as a non-intrusive probe.

A capacitive measuring device according to the invention can also be equipped with a probe of annular geometry 6 comprising, at a first flat end 62 of a tubular part 63, four concentric electrodes and, at its second end, a connector 61, with reference to FIG. 6. These four concentric electrodes comprise two transmitting electrodes 60.1, 60.4 and two receiving electrodes 60.2, 60.3 included between said two transmitting electrodes. This type of probe can also be used as a non-intrusive probe.

In applications requiring intrusive probes, it is possible to provide a probe 7 of tubular type comprising a tubular part 73 upon which two transmitting electrodes 70.1, 70.4 and two electrodes 70.2, 70.3 are disposed, with reference to FIG. 7. The electrical connections between the transmitting and receiving electrodes and the connector 71 of the probe 7 are disposed inside the tubular part 73.

It is also possible to design a probe 8, intended in particular for intrusive measurements, in which transmitting electrodes 80.1, 80.4 and receiving electrodes 80.2, 80.3 are disposed on a flat support 83 integral with a connector 81, with reference to FIG. 8. The two transmitting electrodes 80.1, 80.4 and the two receiving electrodes 80.2, 80.4, located between the two transmitting electrodes, are disposed substantially parallel with each other and are electrically connected to the connector 81 by connecting tracks (not shown) included in the flat support 83.

It should be noted that the probe geometries of the flat-ended, annular, tubular or flat support type that have just been described can apply equally well to probes having four electrodes and to probes having two electrodes.

The conditioner 10 comprises a first measuring connector CP, cooperating with the connector CS of the probe S, and a second interface connector CI.

The measuring connector CS comprising a first contact P1, provided for being electrically connected via the measuring connector CS to a first current injection electrode E1, is connected to the output of an isolating transformer 113 that itself is connected to the output of an oscillator circuit 112 receiving a control signal F via the interface connector CI, this oscillator being at a frequency that is current controlled from outside of the conditioner, and having a constant output amplitude.

A second contact P2 of the measuring connector CP, provided to be electrically connected to one of the voltage measuring electrodes E2, is connected as a positive input to a voltage measuring circuit 13, whilst a third contact P3, provided for being electrically connected to the other voltage measuring electrode E3, is connected as a negative input of said voltage measuring circuit 13.

A fourth contact P4, provided for being electrically connected to the second current injection electrode E4, is connected as a positive input of a current measuring circuit, whilst a fifth contact P5, provided for being electrically connected to a terminal of the measuring resistor 116, is connected as a negative input of the current measuring circuit 14.

A sixth contact P6, provided for being electrically connected to the terminal of the measuring resistor 116, is connected to a floating earth of the secondary of the isolating transformer 113.

The voltage measuring circuit 13 and the current measuring circuit 14, produced in the form of high-impedance differential amplifiers, are designed to deliver respectively a signal V representing the voltage effectively present between the current injection electrodes and a signal I representing the current effectively injected into the fermentation medium, these signals, respectively of voltage and current V, I, being applied as inputs to a circuit for determining electrical characteristics 200.

The conditioner 10 furthermore comprises a power supply module 130, a temperature probe 115 making it possible to correct for the possible thermal drifts of the electronics contained in the conditioner, and a circuit 20 for the electrolytic cleaning of the electrodes of the probe. The conditioner 10 is included in a screening enclosure 100 connected to the earth of the power supply circuit 130 which also constitutes the earth of all of the components of the conditioner with the exception of the secondary winding of the isolating transformer 113.

Figure 2:
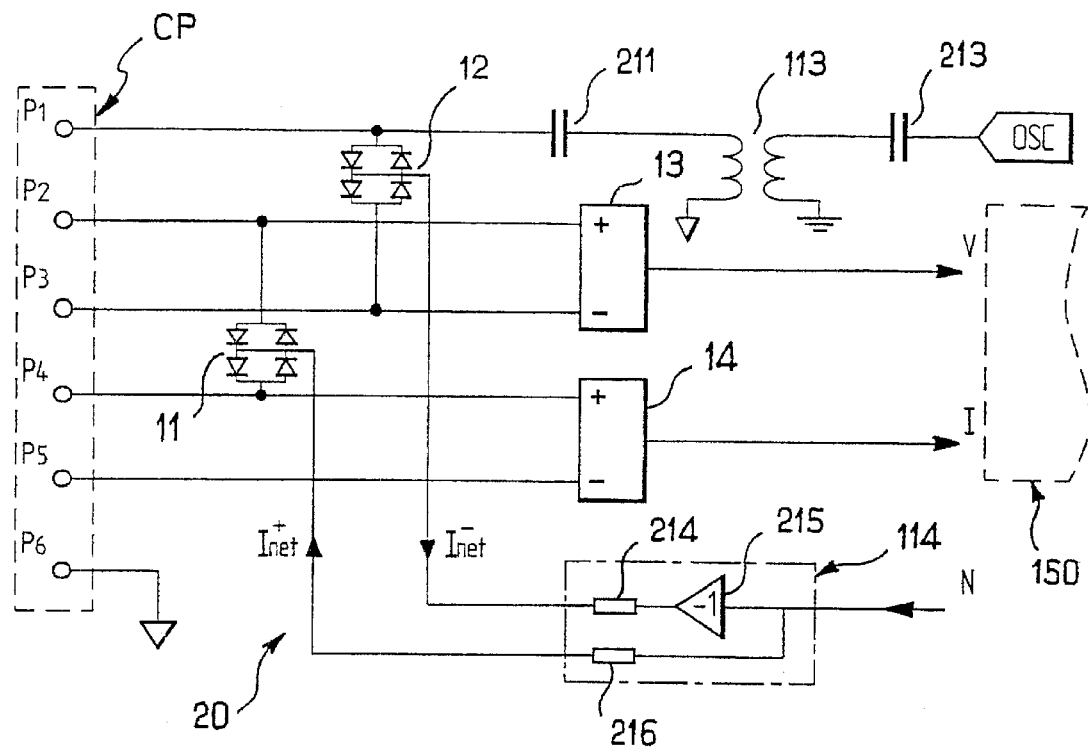
FIG. 2 is a block diagram of a part of the capacitive measuring device shown in FIG. 1.

The cleaning circuit 20 comprises, with reference to FIG. 2, a first group 12 of switching diodes disposed between the output of the isolating transformer 113, through a decoupling capacitor 211, and the negative input of the voltage-measuring differential amplifier 13, a second group 11 of switching diodes disposed between the positive input of the voltage differential amplifier 13 and the positive input of the current-measuring differential amplifier 14, and a cleaning control circuit 114 including a cleaning current injection path $I^{+}_{net}$ through a first limiting resistor 216 and a cleaning current return path $I^{-}_{net}$ through a second limiting resistor 214 and an inverting amplifier 215, these two paths, injection and return, being connected to a cleaning control line N activated from outside of the conditioner 100.

Each group of switching diodes 11, 12 comprises a first set of two diodes connected head-to-tail in series with a second set of two diodes connected head-to-tail, the connecting terminal between the first and second sets of diodes being connected to the cleaning control circuit 114, whilst each of the other terminals of said first and second cleaning sets is connected to a measuring contact of the conditioner 100.

The switching diodes of the two groups 11, 12 are arranged in such a way as to allow the passage of only the DC current used for the electrolytic cleaning of the electrodes of the probe.

The circuit 200 for determining the electrical characteristics of the biomass comprises a device 150 provided for carrying out a null method, this bridge comprising a reference branch on which the current signal I is applied through a first reference resistor $R_I$ corresponding to a reference at a phase of 0 degrees, and two opposing branches on which are respectively applied, on the one hand, the output of a first modulator 15 receiving on its inputs the voltage signal V and an output signal G representing the resistive component of the impedance of the biomass and, on the other hand, the output of a second modulator 16 receiving on its inputs the voltage signal V and the output signal representing the component C.

The output of the first modulator 15 is connected to a terminal of an opposing resistor Ro corresponding to a reference at a phase of 0 degrees.

The output of the second modulator 16 is connected to a terminal of an opposing capacitor of capacity Co corresponding to a reference at a phase of 90 degrees.

It should be noted that the resistors Ro, $R_I$ and the opposing capacitor Co must be chosen to be of high quality in order to guarantee very pure phase references.

The connecting node of the first and second branches of the measuring bridge 150 is connected as an input to an amplifier 17 provided for the null measurement and whose output is applied, on the one hand, to a first synchronous detector 18 though a 90 degree phase shifter ($\pi/2$) and, on the other hand, to a second synchronous detector 19, these two synchronous detectors being controlled by the output of the oscillator 112 and having their respective outputs connected to integrator circuits 110, 111 provided for delivering the output signals C, G respectively representing the capacity and the conductance of the medium. These output signals C, G are respectively applied to control the first and second modulators 15, 16 of the measuring bridge 150.

The control of the first modulator 15 is servo-controlled in such a way that the real part of the impedance is balanced between the reference branch and the opposing branches of the bridge presenting the 0 degree and 90 degree phase references respectively.

The equilibrium is measured by the amplifier 17 and is achieved when its output voltage is zero.

The control of the second modulator 16 is servo-controlled in such a way that there is equilibrium of the imaginary part between the branches of the bridge. This equilibrium is achieved when the output voltage of the amplifier 17 is also zero.

At equilibrium, the respective controls of the first and second modulators 15, 16 are respectively proportional to the measured resistance G and to the measured capacity C.

It should be noted that the impedances Ro, Co and RI respectively recreate the image of the impedances of the circuit of the probe S: Rx, Cx and the measuring resistor 116.

Furthermore, it can be noted that the $\pi/2$ phase shifting circuit takes no part in the measurement of capacity, but is used as a phase corrector to stabilise the servo-control.

It is important to note that in the device according to the invention, it is not necessary to carry out a servo-control of the measurement C of the capacity of the medium, as illustrated in the diagram shown in FIG. 4, in which the determining circuit 40 comprises a reference capacitor Co connected directly in parallel with a reference resistor Ro, the measurement of capacity C being obtained directly at the output of the first synchronous detector 18.

There will now be described a particular example of use of a measuring device according to the invention in order to provide a measurement of the proportion of salt, such as sodium chloride, in a slice of salmon or of ham, with the particular objective of determining the state of freshness of products offered for consumption. Use is made, for example, of a measuring device equipped with a probe of the type having two concentric electrodes made of platinum and having an outside diameter of about 50 mm. The flat end of the probe, on which the two concentric electrodes are disposed, is applied against the upper surface of the tested slice in such a way that the two measuring electrodes come into contact with the biological medium.

The impedance measurement provided by the measuring device according to the invention can be correlated, after calibration, with a value of the proportion of salt in the flesh constituting the slice which is the subject of the measurement. This measurement must in practice be corrected by a measurement of the biomass or of the quantity of flesh.

A measuring device according to the invention can also be used for measuring characteristics of plants, of mushrooms in particular.

The invention is not of course limited to the examples that have just been described and many modifications can be applied to these examples without departing from the scope of the invention. Geometric probe structures other than the one described can thus be envisaged. Furthermore, the determining circuit can comprise other stages for processing the voltage and current signals without by so doing departing from the scope of the present invention.

What is claimed is:

1. Device for determining characteristics of a biomass, comprising:
    a probe (S, S') provided for being applied to a medium containing biological cells, said probe (S, S') comprising means (E1, E4) for injecting a current into said medium, means (E2, E3) for reading the voltage applied to said medium, and means (116) for measuring the injected current,
    a conditioner (10) comprising means (112) for providing a galvanically isolated alternative voltage to be applied to said current injection means (E1, E4), and means (200) for processing signals (I, V) respectively representative of the current injected into said medium and of the voltage read by the voltage reading means (E2, E3), in such a way as to deliver measurement signals (C, G) respectively of the capacity and of the conductance of said medium, characterized in that these processing means (200) comprise:
        a measuring bridge using the null method (150) designed to process a signal representing the injected current and a signal representing the read voltage applied respectively to a reference branch and to two opposing branches, and
        means (15, 16) for automatically controlling this bridge (150) on the basis of the conductance measurement signal (G).

2. Device (1) according to claim 1, characterized in that the measuring bridge (150) comprises:
    a reference branch including a reference resistor to which is applied the signal representing the injected current,
    a first opposing branch including an adjustable opposing resistor and a second opposing branch including an adjustable opposing capacitor, the signal representing the read voltage being applied on these opposing branches, and
    amplification means having their input connected to said reference and opposing branches and delivering a null measurement signal.

3. Device (1) according to claim 2, further comprising means (13) of delivering a signal representing the voltage read by the voltage reading means and means (14) of delivering a signal representing the current injected by the current injection means, characterized in that the conditioner (10) further comprises a first modulator (15) inserted between the output of the means (13) of delivering the signal representing voltage and the first opposing branch, said first modulator (15) being controlled by the conductance measurement signal (G) in such a way that the null measurement signal is substantially zero.

4. Device (1) according to claim 1, characterized in that the probe (S) comprises four wires (F1, F2, F3, F6) connecting the current injection means and the voltage reading means to four terminals of connection means (CS) for connecting with the conditioner, and two additional wires (F4, F5) respectively connecting the terminals of a current measuring resistor (116) disposed inside said probe (S) to two other terminals of said connection means (CS).

5. Device according to claim 4, characterized in that the current injection means comprise two current electrodes (E1, E4) for injecting current into the medium and the voltage reading means comprise two voltage electrodes (E2, E3) for reading the voltage applied to the medium.

6. Device (1) according to claim 5, characterized in that the current measuring resistor (116) is inserted between one of the current injection electrodes (E4) and one (F6) of the wires of the probe (S) connected via the connection means (CS) to a floating earth of the conditioner (10).

7. Device according to claim 6, characterized in that the probe (S) further comprises a compensating resistor (117) inserted between one wire of the probe (S) and the other current injection electrode (E1).

8. Device according to claim 4, characterized in that the current injection means and the voltage reading means are produced in the form of a pair of measuring electrodes (E1', E2') comprising a first measuring electrode (E1') connected to both a first wire and a second wire (F1, F2) of the probe (S') and a second measuring electrode (E2') connected to both a third wire and a fourth wire (F3, F4) of the probe (S').

9. Device according to claim 8, characterized in that the current measuring resistor (116) is inserted between the second measuring electrode and one (F6) of the wires of the probe (S') connected via the connecting means (CS) to a floating earth of the conditioner (10).

10. Device according to claim 9, characterized in that the probe (S') further comprises a compensating resistor (117) inserted between the first measuring electrode (E1') and a wire (F1) of the probe.

11. Device (1) according to claim 5, characterized in that the current measuring resistor (116) is disposed in the vicinity of the electrodes (E1–E4; E1', E2') of the probe (S).

12. Device according to claim 5, characterized in that the electrodes (50.1, 50.2, 50.3, 50.4) are disposed on a flat support (52) at the end of a cylindrical body (53) of the probe (S).

13. Device according to claim 12, characterized in that the electrodes (50.1, 50.2, 50.3, 50.4) are disposed substantially parallel with each other.

14. Device according to claim 12, characterized in that the electrodes (60.1, 60.2, 60.3, 60.4) are concentric annular elements.

15. Device according to claim 5, characterized in that the probe (7) comprises a tubular body (73) about which the electrodes (70.1, 70.2, 70.3, 70.4) are disposed.

16. Device according to claim 5, characterized in that the probe (8) comprises a substantially flat body (83) upon which the electrodes (80.1, 80.2, 80.3, 80.4) are disposed.

17. Device (1) according to claim 1, characterized in that the automatic control means are further designed to control the measuring bridge (150) on the basis of the capacity measurement signal (C).

18. Device (1) according to claim 17, characterized in that the conditioner (10) further comprises a second modulator (16) inserted between the output of the means (13) of delivering the signal representing voltage and the opposing capacitor (Co), said second modulator (16) being controlled by the capacity measuring signal (C) in such a way that the null measuring signal is substantially zero.

19. Device (1) according to claim 1, characterized in that the processing means further comprise, at the output of the measuring bridge (150), a first channel and a second channel respectively, each one comprising synchronous detection means (18, 19) and integrator means (110, 111) delivering the capacity and conductance measurement signals (C, G) respectively, said synchronous detection means (18, 19) being controlled by the output signal of oscillator means (112).

20. Device (1) according to claim 1, characterized in that the probe (S) comprises only passive components and is connected in a detachable manner to the conditioner (10).

21. Device according to claim 1, characterized in that the probe comprises at least one active component and is connected in a detachable manner to the conditioner.

22. Device (1) according to claim 20, characterized in that the conditioner (10) further comprises a first differential amplifier and a second differential amplifier (13, 14) electrically connected to the probe (S) and provided for delivering the signal representing current (I) and the signal representing voltage (V) respectively.

23. Device (1) according to claim 1, characterized in that the conditioner (10) further comprises means (11, 12, 114) for carrying out an electrolytic cleaning of the electrodes (E1–E4).

24. Device according to claim 1, characterized in that the conditioner (10) further comprises temperature probe means (115) within said conditioner (10).

25. Method for determining characteristics of a biomass, embodied in the device according to claim 1, comprising:

an injection of an alternative current, at a predetermined frequency into a medium containing biological cells, by current injection means, a measurement of the current injected into said medium, a measurement of the current injected into said medium, a measurement of the voltage applied to said medium by voltage reading means, disposed in the vicinity of the current injection means, a processing of the signals representing the current injected into said medium and the read voltage respectively, in such a way as to deliver measurement signals of the capacity and of the resistance respectively of said medium, characterised in that the processing of the current and voltage signals includes a null method using a measuring bridge comprising a reference branch including a reference resistor, on which the signal representing the current is applied, and two opposing branches respectively comprising an adjustable resistive component and an adjustable capacitive component, and this measuring bridge being automated to deliver respectively a measurement signal of capacity and a measurement signal of conductance of the medium.

26. Method according to claim 25, characterized in that the device comprises a first servo-control of the measuring bridge by means of the conductance measuring signal.

27. Method according to claim 25, characterized in that the device comprises a second servo-control of the measuring bridge by means of the capacity measuring signal.

28. The device according to claim 1, for measuring a proportion of salt in a medium containing biological cells.

29. The device according to claim 28, wherein the measurement of proportion of salt is corrected by a biomass measurement.

* * * * *